(12) United States Patent
Chen et al.

(10) Patent No.: US 7,713,201 B2
(45) Date of Patent: May 11, 2010

(54) METHOD AND APPARATUS FOR SHEAR PROPERTY CHARACTERIZATION FROM RESONANCE INDUCED BY OSCILLATORY RADIATION FORCE

(75) Inventors: Shigao Chen, Rochester, MN (US); James F. Greenleaf, Rochester, MN (US); Mostafa Fatemi, Rochester, MN (US)

(73) Assignee: Mayo Foundation for Medical Education, Rochester, MN (US)

( * ) Notice: Subject to any disclaimer, the term of this patent is extended or adjusted under 35 U.S.C. 154(b) by 1269 days.

(21) Appl. No.: 10/821,461

(22) Filed: Apr. 9, 2004

(65) Prior Publication Data

US 2005/0004463 A1    Jan. 6, 2005

Related U.S. Application Data

(60) Provisional application No. 60/461,605, filed on Apr. 9, 2003.

(51) Int. Cl.
*A61B 8/00* (2006.01)

(52) U.S. Cl. .................. 600/438; 600/439; 600/442; 600/437; 601/2; 606/128; 73/1.82; 73/1.89

(58) Field of Classification Search ............ 600/437, 600/442, 443, 439; 73/801, 778, 579, 573, 73/1.82, 1.89; 601/2; 606/128
See application file for complete search history.

(56) References Cited

U.S. PATENT DOCUMENTS

| | | | |
|---|---|---|---|
| 5,099,848 A | 3/1992 | Parker et al. | |
| RE34,663 E * | 7/1994 | Seale | 600/587 |
| 5,474,070 A | 12/1995 | Ophir et al. | |
| 5,524,636 A | 6/1996 | Sarvazyan et al. | |
| 5,606,971 A * | 3/1997 | Sarvazyan | 600/438 |
| 5,678,565 A | 10/1997 | Sarvazyan | |
| 5,706,815 A | 1/1998 | Sarvazyan et al. | |
| 5,810,731 A | 9/1998 | Sarvazyan et al. | |
| 5,833,633 A | 11/1998 | Sarvazyan | |
| 5,860,934 A | 1/1999 | Sarvazyan | |
| 6,068,597 A * | 5/2000 | Lin | 600/443 |
| 6,385,474 B1 | 5/2002 | Rather et al. | |
| 6,468,215 B1 * | 10/2002 | Sarvazyan et al. | 600/438 |
| 6,468,231 B2 | 10/2002 | Sarvazyan et al. | |
| 6,875,176 B2 * | 4/2005 | Mourad et al. | 600/442 |
| 2002/0095087 A1 * | 7/2002 | Mourad et al. | 600/442 |
| 2004/0077949 A1 * | 4/2004 | Blofgett et al. | 600/472 |
| 2005/0283072 A1 * | 12/2005 | Qin et al. | 600/437 |

OTHER PUBLICATIONS

S. Chen, et al., "Vibro-acoustography of Small Spheres," Ultrasound Research Laboratory, Mayo Clinic [Date??] (Presentation).

A.P. Sarvazyan, et al., "Shear Wave Elasticity Imaging: A New Ultrasonic Technology of Medical Diagnostics," Ultrasound in Med. Biol. 24(9):1419-1435, 1998.

* cited by examiner

*Primary Examiner*—Brian Casler
*Assistant Examiner*—Joel M Lamprecht
(74) *Attorney, Agent, or Firm*—Quarles & Brady LLP

(57) ABSTRACT

A method for determining a shear elasticity and shear viscosity of a material based on resonance characteristics. A focused ultrasound wave is directed at the material to induce oscillations in the material, and a velocity of the material is measured. A spectrum of frequency of oscillation versus velocity is developed, and the resonance characteristics exhibited by the spectrum are used to estimate the shear elasticity and viscosity of the material.

24 Claims, 2 Drawing Sheets

METHOD AND APPARATUS FOR SHEAR PROPERTY CHARACTERIZATION FROM RESONANCE INDUCED BY OSCILLATORY RADIATION FORCE

CROSS-REFERENCE TO RELATED APPLICATION

This application claims priority to provisional application Ser. No. 60/461,605, filed Apr. 9, 2003, incorporated by reference herein.

STATEMENT REGARDING FEDERALLY SPONSORED RESEARCH OR DEVELOPMENT

This work was supported by grant HL61451 from the National Institutes of Health and grant DAMD 17-98-1-8121 from the Department of Defense.

BACKGROUND OF THE INVENTION

The present invention relates to a method and apparatus for determining shear elasticity and shear viscosity of a material, and more particularly to a method for determining the shear elasticity and shear viscosity of a material based on resonance spectra of the medium under test.

The study of objects in terms of their mechanical response to external forces is of considerable interest in material science and medical diagnosis. Changes of elasticity of soft tissues are often related to pathology, and therefore the study of and characterization of changes in elasticity of materials can be an important diagnostic tool.

Traditionally, the mechanical characteristics of tissue have been examined through palpation. Palpation is a process in which a static force is applied to tissue and an estimation of the tissue elasticity is made through the sense of touch. While providing some information regarding the characteristics of the tissue, this method is highly dependent on the opinion of the medical practitioner estimating the force, and, although often useful, is not repeatable and does not provide a useful scale for characterizing the tissue.

Another prior art method for characterizing the mechanical properties of tissue is elasticity imaging, which has been the subject of extensive investigation in recent years. Elasticity imaging provides a quantitative method for measuring the mechanical properties of tissue. Generally, an excitation force is applied to the tissue and the response of the tissue is used to reconstruct the elastic parameters of the tissue. These parameters are typically related to the shear modulus, or "hardness" of the tissues being imaged. While providing a means for repeatably characterizing tissue, however, the ability of conventional B mode ultrasound imaging to differentiate various tissues depends principally on the acoustic impedance, which in turn depends upon the bulk modulus of the tissue under examination. The range of variation of bulk modulus, however, is relatively small. Therefore, the bulk modulus does not vary sufficiently as a function of the state of the tissue to allow for a characterization of the tissue.

Recently, vibro-acoustography, a method that can image the "hardness" of an object, has been developed. In vibro-acoustography, a confocal transducer having a center disk and an outer ring introduces two ultrasound beams to the same focal spot in an object. The two ultrasound beams have slightly different frequencies: for example, 1.001 MHz, and 0.999 MHz. At the focal spot, the interference of these two beams causes the object to vibrate at the beat frequency, in this example, at 2 kHz. Acoustic emissions from the object are detected by an acoustic hydrophone. These emissions contain information about the local material properties of the object.

By scanning the focal plane of the transducer in a raster manner, a 2D image of the object can be generated. In this method, the applied force is oscillative, allowing the dynamic properties of the material to be examined. The force is also confined to a local spot, therefore providing good spatial resolution of the image. This method is therefore particularly useful in detecting hard inclusions in soft material. For example, it has been used to image calcification in human arteries, microcalcification in breast tissue, and fractures in metal parts.

In vibro-acoustography, the brightness of a pixel is related to the stiffness and reflectivity of that location. However, the image is not a direct representation of a single elastic modulus. Rather, it combines information about several material properties of the object. Therefore, present versions of vibro-acoustography do not provide a direct evaluation of the stiffness of a material under examination.

SUMMARY OF THE INVENTION

The present invention is a method for characterizing an elasticity property of a viscous medium. A focused ultrasound wave is directed at the viscous medium to produce a vibrational force on the medium, and a vibrational velocity of the medium is determined as a function of the frequency of vibration. These steps are repeated over a range of frequencies to develop a velocity versus frequency spectrum of the medium. A resonant frequency is determined, and the resonant frequency and/or the resonant spectrum are used to determine an elasticity property of the medium, and can be used to determine or estimate at least one of a shear elasticity or a shear viscosity.

In another aspect of the invention, an apparatus for determining an elasticity property of a viscous medium is provided. The apparatus includes an ultrasound transducer for applying an ultrasound beam operating at a selectively varying frequency at the viscous medium, and a detector for measuring a velocity and a frequency of vibration of the medium as the ultrasound wave is applied. A processing unit is electrically connected to the transducer to drive the transducer to emit waves at varying frequencies over a selected frequency range, and to the detector to receive the velocity of vibration from the detector, the frequency and velocity providing coordinates for a resonance profile. Based on the resonance profile, the processing unit determines at least one of a shear elasticity and a shear viscosity. The transducer can be directed at various positions in the medium, and the shear elasticity and shear viscosity determined at multiple locations in order to characterize variations in the medium.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE PREFERRED EMBODIMENT

The present invention comprises a method for characterizing material properties of a viscous medium as a function of a resonance of a velocity of vibration in the medium when subjected to an applied stimulating oscillatory force. A profile of vibration velocity versus frequency is developed, and the resonant frequency of the medium is evaluated. The derived profile and resonant frequency are used to characterize the shear properties of the viscous medium, including both shear modulus and shear viscosity. The range of values of the shear modulus and viscosity of a tissue is substantially greater than that of prior art methods which relied, for example, on bulk modular parameters, and therefore provide an improved diagnostic value over bulk modulus methods.

Theory

Figure 1:
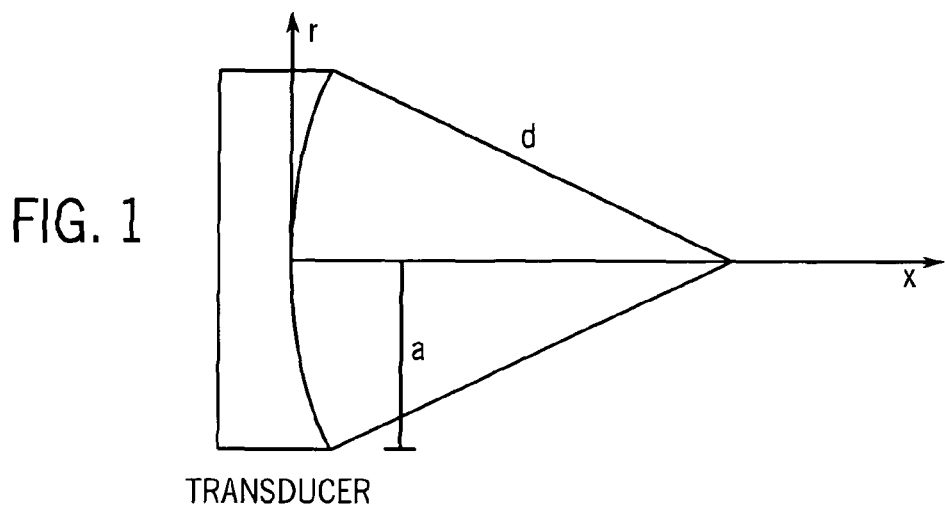
FIG. 1 is an illustration of an ultrasound transducer showing various coordinates.

The displacement of a homogeneous medium along the axis of sound propagation (x component) due to a radiation force applied by a focused transducer operating in an amplitude modulating mode, e.g., $Sin(\Omega t)Sin(\omega_0 t)$ is:

$$S_x = \frac{\alpha a^2 I_0}{2c\rho} e^{-2\alpha x}$$

$$\int_0^\infty \frac{\text{Exp}\left[\frac{-a^2 f^2 \beta^2}{8}\right] J_0(\beta r)\beta}{\sqrt{(\beta^2 c_t^2 - \Omega^2)^2 + (\Omega \beta^2 v)^2}} \text{Sin}\left(\Omega t - \arctan\frac{\Omega \beta^2 v}{\beta^2 c_t^2 - \Omega^2}\right) d\beta,$$

where α and c are the attenuation and speed of ultrasound, ρ is the density of the medium $I_0$ is the intensity of ultrasound at the beam axis, $v = \eta/\rho$ is the kinematic shear viscosity, $c_t$ is the shear sound speed (mathematically related to the shear elasticity) of the medium, $J_0$ is First kind Bessel function of order zero, β is the dummy variable for integration, a is the radius of the transducer (FIG. 1), x is the direction of propagation of sound. These equations can be found, for example, in Ultrasound in Medicine & Biology, 24:1419-1435, 1998, A. P. Sarvazyan, et al., which is incorporated herein by reference for its description of this equation. The transducer coordinates are shown in FIG. 1, where the radius is a, the direction of propagation x, and the distance to the focus of the transducer is d.

For harmonic vibration, the velocity is equal to the displacement times the frequency of vibration.

$$V_x = S_x \cdot \Omega.$$

A relationship therefore exists between the vibration of velocity and the shear parameters of the medium in which the wave is produced.

Figure 2:
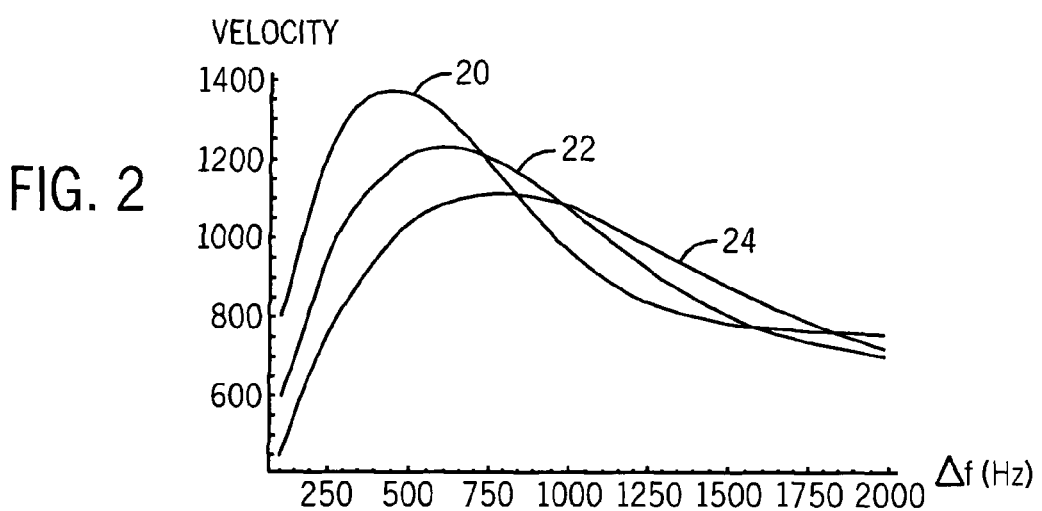
FIG. 2 is a chart illustrating velocity versus frequency resonance spectra for a computer simulation of a homogeneous medium having a fixed shear viscosity and varying shear elasticities.
Figure 3:
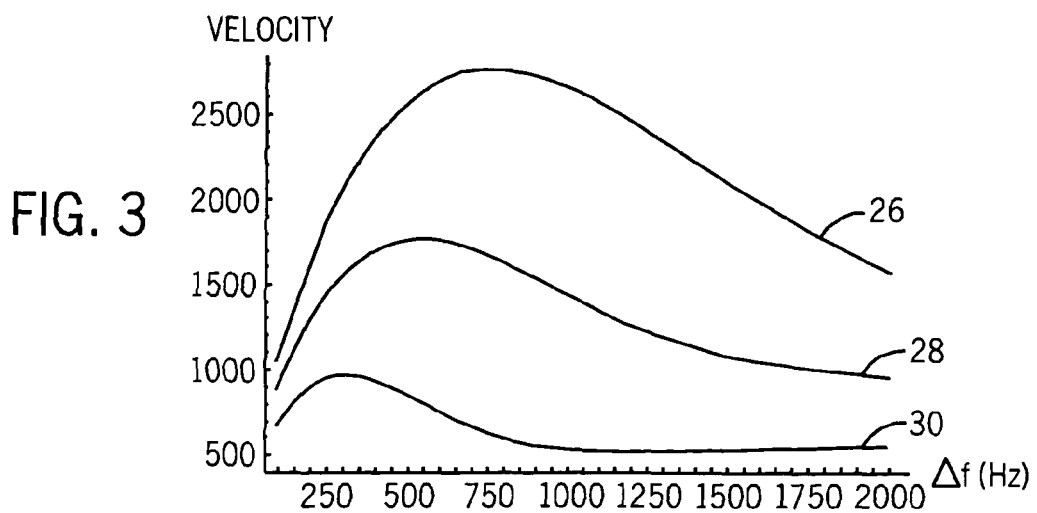
FIG. 3 is a chart illustrating velocity versus frequency resonance spectra for a computer simulation of a homogeneous medium having a fixed shear elasticity and varying shear elasticities.

Referring now to FIGS. 2 and 3, graphs illustrating the results of computer simulations of the amplitude of vibration velocity at the focus of the transducer, for a transducer having a radius a=5 cm, a geometric focus d=8 cm, and a center frequency of 1.5 MHz are shown. Referring first to FIG. 2, a simulation was produced for a homogeneous medium having a fixed shear viscosity of 0.5 Pa*s and a varying shear elasticity of 4, 6.25, and 9 kPa for each of the curves 20, 22, and 24, respectively. Under these conditions, each of the velocity curves exhibits a resonant frequency, and the resonant frequency increases as the medium becomes less elastic or more stiff. Referring now to FIG. 3, here the shear elasticity is fixed at 4 kPa and the shear viscosity for the curves 26, 28, and 30 is varied, the shear viscosity for the curves being provided at 0.1, 0.5 and 1 Pa*s, respectively. Here, again, each of the curves 26, 28, and 30 exhibits resonance. Here the resonance decreases with increased viscosity. The resonance profile, therefore, is related to the shear viscosity and the shear elasticity, and can be used to determine or estimate these parameters.

Operation

Figure 4:
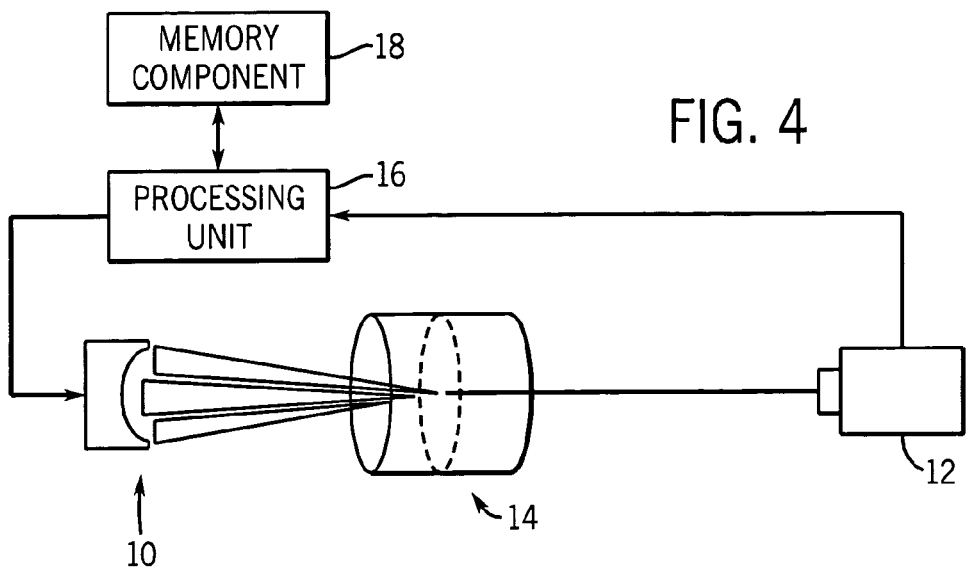
FIG. 4 is a block diagram of a system for performing the method of the invention.

Referring now to FIG. 4, an apparatus for determining elasticity parameters, particularly a shear viscosity and a shear elasticity of a medium under test is shown. The apparatus comprises a focused ultrasound transducer 10, directed at a medium 14, and a detector 12, here a laser vibrometer, such as, for example, those disclosed in U.S. Pat. No. 5,159,416 to Adler or U.S. Pat. No. 5,495,767 to Wang, which are hereby incorporated by reference for their description of such devices. The focused ultrasound transducer 10 is directed at the medium 14 to be tested, and the laser vibrometer 12 is positioned to receive a reflected signal for detecting the velocity of vibration at the focal point of the transducer 10 in the medium. As described above, the transducer 10 applies a focused ultrasound wave, preferably an amplitude modulated wave, oscillating at a frequency of less than 5 kHz. The applied wave is a continuous ultrasound wave whose amplitude is modulated sinusoidally.

Here, the medium 14 is a homogeneous transparent gel including a layer of white paint to provide a reflective surface for laser measurement by the vibrometer 12. The width of the layer of paint is selected to be sufficiently wide to allow reflection, but sufficiently thin such that the effects of the paint can be ignored in the results. The focus of the transducer 10 is focused at the paint layer. The velocity of vibration at the focus of the transducer 10 is detected by the laser vibrometer 12.

Figure 5:
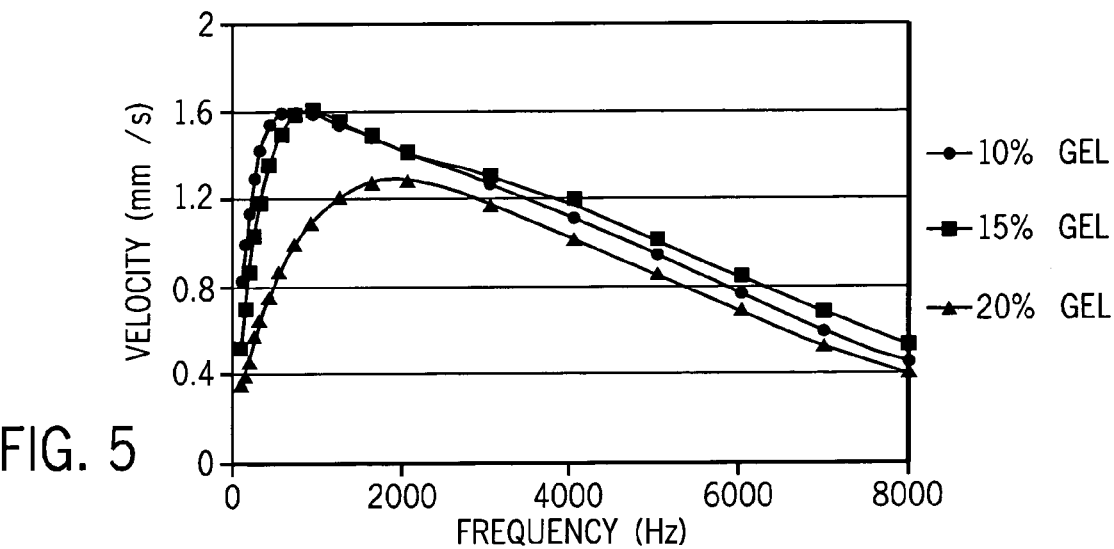
FIG. 5 is a velocity spectra illustrating resonance for homogeneous gels having varying degrees of stiffness.

To determine a shear viscosity or shear elasticity of the medium 14 under test, a processing unit or computer device 16 selectively drives the transducer 10 to produce a plurality of ultrasound waves at varying frequencies over a selected frequency range which can be, as shown in FIG. 5, between zero and 8 kHz. As described above, the applied wave is continuous, and has an amplitude which varies sinusoidally. Velocity readings are acquired corresponding to the selected frequency steps. The frequency and velocity coordinates are stored in a memory component 18 as coordinate points in a velocity versus frequency resonance spectrum. The resonance spectra and/or resonant frequency data can be compared against known data stored in a data structure in the memory component 18 to determine the shear properties of the medium under test. For a homogenous medium 14 as described, data can be acquired at a single location in the medium 14. For a non-homogenous material, spectra data can be gathered for various locations throughout the medium to characterize, for example, variations in a tissue sample. Such a method can be used, for example, to evaluate calcification and to biopsy tissue.

Referring again to FIG. 5, a chart illustrating the velocity versus frequency spectra for three different homogeneous mediums having gel concentrations of 10%, 15%, and 20% respectively, and therefore having increasing stiffness characteristics are shown. For each of the gel phantoms, the frequency of the applied vibration of the transducer 10 is shown as varied over a range between zero and 8 kHz, along with the corresponding velocity readings acquired by the detector 12. The velocity spectra for each of the gel concentrations show resonance, with the resonant frequency increasing as the medium 14 becomes stiffer (i.e., with a higher concentration of gelatin). As described above, the shear elasticity and viscosity can be determined by comparison of the collected data to a resonance profile or to known resonant frequencies. This method can be used therefore, to estimate the shear properties of the medium.

Figure 6:
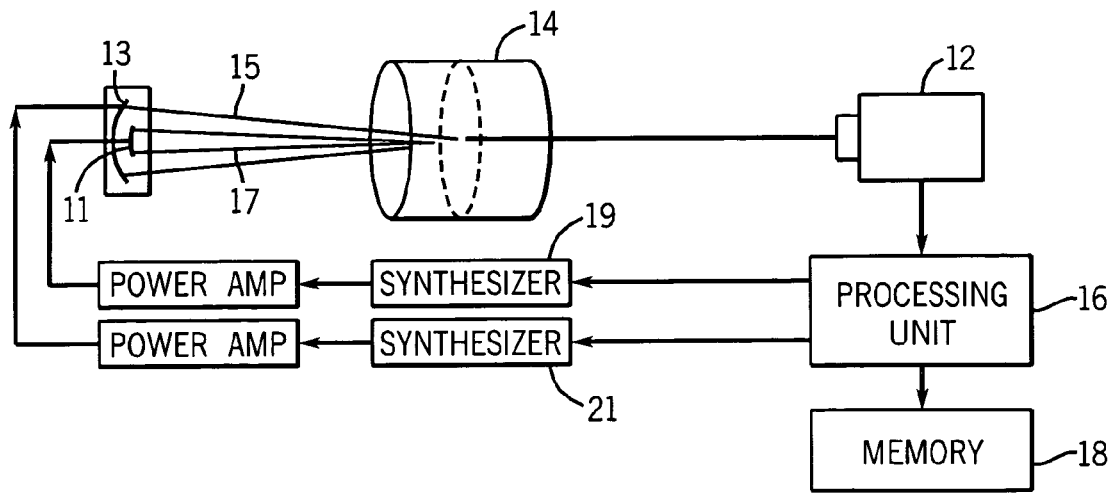
FIG. 6 is a block diagram of a second embodiment of a system for performing the method of the present invention.

Referring now to FIG. 6, the focused ultrasound transducer 10 can also be a confocal transducer comprising two elements 11 and 13 which produce two focused beams 15 and 17 that cross each other at their focal points, as described in U.S. Pat. No. 5,991,239 to Fatemi-Boosheri, et al., which is hereby incorporated herein by reference for its description of such devices. The elements 11 and 13 can be driven by continuous wave synthesizers 19 and 21, or by other methods as described in the cited reference, at ultrasound frequencies $f_1$ and $f_2$ producing a beat force having a frequency $\Delta f = f_1 - f_2$. As described above with reference to FIG. 4, the transducer can be driven by a processing unit or computer device 16 to drive the confocal transducer to produce ultrasound waves at varying frequencies. While a confocal transducer is shown here, transducers which produce two or more ultrasound beams with different frequencies can also be applied, irrespective of whether the beams are confocal.

Although the invention has been described with reference to an analysis in which the medium is a transparent homogeneous gel, the method described can also be applied to opaque mediums and both homogeneous and non-homogeneous media. The detector, although shown as a laser vibrometer suitable for use with a transparent material, can be provided using an ultrasound based motion detector, such as those described in Shukui Zhao, Yi Zheng, Shigao Chen, and James F. Greenleaf, "High Sensitivity Vibration Amplitude Estimation using Pulse Echo Doppler Ultrasound," Proceedings of 2003 IEEE International Ultrasonic Symposium, 1923-1926; Yi Zheng, Shigao Chen, Wei Tan, and James F. Greenleaf, "Kalman Filter Motion Detection for Vibro-acoustography," Proceedings of 2003 IEEE International Ultrasonic Symposium, 1812-1815, which are hereby incorporated by reference for their description of these devices, or a Magnetic Resonance Elastography system, such as that described in U.S. Pat. No. 5,592,085, which is incorporated herein by reference for its description of the MRE method. Each of these systems enable the measurement of motion at the focus of the transducer in the medium. Furthermore, although the apparatus is shown using a focused transducer producing an amplitude modulated ultrasound wave, other methods for vibrating the medium.

It should be understood that the methods and apparatuses described above are only exemplary and do not limit the scope of the invention, and that various modifications could be made by those skilled in the art that would fall under the scope of the invention. To apprise the public of the scope of this invention, the following claims are made:

The invention claimed is:

1. A method for characterizing an elasticity property of a viscous medium, the method comprising:
    (a) directing an ultrasound wave in the viscous medium and modulating the ultrasound wave at a frequency of vibration to produce a vibrational force on the medium at a focal point of the transducer inducing a vibration of the medium at the frequency of vibration;
    (b) determining a vibrational velocity of the medium at the focal point of the transducer as a function of the frequency of vibration;
    (c) repeating steps (a) and (b) for a plurality of frequencies to develop a resonance spectrum of the medium;
    (d) determining a resonance frequency of the viscous medium; and
    (e) determining the elasticity property from the resonance spectrum at the focal point of the transducer.

2. The method as defined in claim 1, wherein the step of modulating the ultrasound wave comprises modulating an amplitude of the ultrasound wave.

3. The method as defined in claim 1, wherein the ultrasound wave is a confocal ultrasound wave.

4. The method as defined in claim 1, wherein the ultrasound wave comprises ultrasound waves produced by a plurality of ultrasound sources.

5. The method as defined in claim 1, wherein step (e) comprises comparing the resonance spectrum to at least one stored resonance spectrum.

6. The method as defined in claim 1, wherein step (b) comprises sensing the vibrational motion of the medium with a laser vibrometer.

7. The method as defined in claim 1, wherein step (b) comprises sensing the vibrational motion of the medium with an ultrasound based motion detector.

8. The method as defined in claim 1, wherein the elasticity property comprises at least one of a shear modulus or a shear viscosity of the medium.

9. The method as defined in claim 1, wherein the viscous medium is a biological tissue.

10. A method for characterizing tissue, the method comprising the following steps:
    (a) directing a ultrasound wave modulated at a first oscillating frequency from an ultrasound transducer at a focal point of the transducer in the tissue to induce a vibration in the tissue at the focal point of the transducer;
    (b) measuring a velocity of the vibration in the tissue at the focal point of the transducer;
    (c) varying the oscillating frequency over a range selected to produce a resonance spectrum correlated to a response in the tissue at the focal point of the transducer; and
    (d) correlating the resonance spectrum to a known elasticity parameter associated with the resonant frequency.

11. The method as defined in claim 10, further comprising the step of varying the focal point across a selected portion of tissue to characterize changes in the tissue.

12. The method as defined in claim 11, further comprising the step of differentiating a first type of tissue from a second type of tissue.

13. The method as defined in claim 12, wherein one of the first and second types of tissue is a calcification.

14. The method as defined in claim 10, further comprising the step of varying the oscillating frequency in a range between zero and eight kilohertz.

15. An apparatus for determining a elasticity property of a viscous medium, the apparatus comprising:
  (a) an ultrasound transducer for applying an ultrasound beam modulated at a selectively varying frequency at the viscous medium to induce a vibration in the viscous medium at a focal point of the ultrasound transducer;
  (b) a detector for measuring a velocity and a frequency of the vibration of the medium at the focal point of the transducer; and
  (c) a processing unit, the processing unit electrically connected to:
    (i) drive the ultrasound transducer to modulate the ultrasound waves at varying frequencies over a selected frequency range;
    (ii) receive the velocity and frequency of vibration from the detector;
    (iii) determine a resonant frequency at selected positions within the medium; and
    (iv) determine at least one of a shear elasticity and a shear viscosity as a function of the resonance spectrum at the focal point of the transducer.

16. The apparatus as defined in claim 15, further comprising a memory component connected to the processor for storing a resonance spectrum profile correlating the vibrational velocity of the medium versus the frequency of vibration of the medium.

17. The apparatus as defined in claim 16, wherein the memory component further comprises a data structure storing known resonance spectrum and correlating the known resonance spectrum to at least one of a shear modulus and a shear viscosity.

18. The apparatus as defined in claim 15, wherein the transducer produces an amplitude modulated signal.

19. The apparatus as defined in claim 15, wherein the transducer is a confocal transducer.

20. The apparatus as defined in claim 15, wherein the detector is a magnetic resonance elastography system.

21. The apparatus as defined in claim 15, wherein the detector is an ultrasound based motion detector system.

22. The method as recited in claim 1, wherein the frequency of vibration caused by the vibrational force is varied between zero and eight kilohertz.

23. The method as recited in claim 10, wherein the known elasticity parameter comprises at least one of a shear modulus and a shear viscosity.

24. The apparatus as recited in claim 15, wherein the selected frequency range is in a range between zero and eight kilohertz.

* * * * *